(12) United States Patent
Terzian et al.

(10) Patent No.: US 8,883,176 B2
(45) Date of Patent: Nov. 11, 2014

(54) SMOOTH, HIGH SOLIDS TABLET COATING COMPOSITION

(75) Inventors: Lana L. Terzian, Middletwon, NY (US); Stuart C. Porter, Hatfield, PA (US)

(73) Assignee: ISP Investments Inc., Wilmington, DE (US)

( * ) Notice: Subject to any disclaimer, the term of this patent is extended or adjusted under 35 U.S.C. 154(b) by 150 days.

(21) Appl. No.: 13/062,807

(22) PCT Filed: Sep. 24, 2009

(86) PCT No.: PCT/US2009/058177
§ 371 (c)(1),
(2), (4) Date: Apr. 25, 2011

(87) PCT Pub. No.: WO2010/036777
PCT Pub. Date: Apr. 1, 2010

(65) Prior Publication Data
US 2011/0189245 A1    Aug. 4, 2011

Related U.S. Application Data

(60) Provisional application No. 61/100,036, filed on Sep. 25, 2008.

(51) Int. Cl.
| | | |
|---|---|---|
| *B05D 3/00* | (2006.01) | |
| *A61P 43/00* | (2006.01) | |
| *A61K 9/00* | (2006.01) | |
| *A61K 47/38* | (2006.01) | |
| *A61K 9/28* | (2006.01) | |

(52) U.S. Cl.
CPC ............... *A61K 9/282* (2013.01); *A61K 9/284* (2013.01); *A61K 9/2866* (2013.01); *A61K 9/286* (2013.01)
USPC .................. 424/400; 427/2.14; 514/781

(58) Field of Classification Search
USPC ........................................................ 424/400
See application file for complete search history.

(56) References Cited

U.S. PATENT DOCUMENTS

| | | | |
|---|---|---|---|
| 6,432,448 B1 * | 8/2002 | Augello et al. ............... | 424/479 |
| 2004/0001884 A1 * | 1/2004 | Moroni et al. ................ | 424/465 |
| 2004/0052844 A1 * | 3/2004 | Hsiao et al. ................... | 424/471 |
| 2007/0026083 A1 * | 2/2007 | Doney .......................... | 424/490 |
| 2007/0141150 A1 * | 6/2007 | Kandarapu et al. .......... | 424/472 |
| 2007/0224260 A1 * | 9/2007 | Mehta et al. .................. | 424/452 |

* cited by examiner

*Primary Examiner* — Audrea Buckley
(74) *Attorney, Agent, or Firm* — Thompson Hine LLP; William J. Davis

(57) ABSTRACT

The invention describes a coating composition comprising an effective amount of a water-soluble cellulose ether, a poly(N-vinyl pyrrolidone-co-vinyl acetate) copolymer, a film-forming agent based on D-glucose, and a plasticizer.

7 Claims, 17 Drawing Sheets

SMOOTH, HIGH SOLIDS TABLET COATING COMPOSITION

FIELD OF THE INVENTION

The current invention relates to coating compositions, and the methods of coating solid substances, e.g., tablet, granules, lozenges, candy, seeds, and the like, with these coating compositions, and the products thus produced.

DESCRIPTION OF PRIOR ART

Coatings play important roles in many industry segments, including (in alphabetical order): agricultural, automotive, biochemical, chemical, computer, consumer goods, foods, electronics, health care, materials, nutritional, pharmaceutical, and veterinary. The ubiquity of coatings across so many application arts is due to the wide range of functionality they impart, such as: protection (e.g., from water absorption, ultra-violet damage), separation (e.g., chemical incompatibilities), altered release of active ingredients (e.g., immediate, extended, delayed, controlled release), and modification of the sensory perception (e.g., smoothness/roughness, taste, color).

A coating can be defined as a layer that covers a surface, especially a solid surface. This layer may be homogeneous or heterogeneous in composition, and vary in uniformity and continuity. Indeed, additional coatings or materials may be placed on top of a coating. Due to the great variety of coatings applications, an extensive array of methods has been developed for applying coatings to the recipient surface. Examples of these methods are well known to one skilled in the arts, and include (in alphabetical order): blade metering, brush coating, dip coating, electrodeposition, film coating, roller coating, and spray coating.

The current invention describes coating compositions and the coated products that are particularly well-suited for the agricultural, nutritional, pharmaceutical, and veterinary industries due to their exceedingly low toxicity, and methods used to produce them. In preferred embodiments, these coatings may find use in oral (e.g., buccal, sublingual, ingested), rectal, and vaginal dosage forms. Such coatings may serve an aesthetic purpose, meaning they improve the appearance of the coated product (e.g., color, gloss, and smoothness), and/or provide an immediate release to the active ingredient, meaning the coatings do not substantially control, delay, extend, or modify the release of active compared to an equivalent, uncoated product.

The novelty of the current invention is better understood by describing the performance features demanded from an ideal coating. Such a coating provides superior performance from the coating preparation, through the coating application process, and to the final product performance. Each of these areas presents challenges to the formulation scientist.

First, ready-made coating systems are highly preferred within the industry, avoiding the customization of coating formulations by the end-user that can lead to purchasing complications and variability in product quality. The ready-made coating system should be provided as a dry powder that can be stored under ambient temperatures and relative humidities. Such a coating must be easy to prepare in a simple solvent system that preferably is water-based, or even more preferably, uses water as the sole solvent. Coating systems that require non-aqueous solvents or special pre-mix processing steps should be avoided. The dry powder should disperse and dissolve readily, without producing clumps, fish-eyes, or foam, and should not leave grit that can foul the filter or block the spray nozzle.

The coating step, typically performed by spray coating, represents the next test of the coating quality. The coating liquid must possess sufficiently low viscosity to enable trouble-free pumping and atomization by the coating nozzles (also called guns). Coating liquids that are too viscous, which can be caused by improper choice of ingredients or too high solids content, can lead to nozzle bearding and clogging, which can be time-consuming to resolve, and cause problems with effective atomization of the coating liquid. An ideal coating liquid atomizes cleanly and remains sufficiently fluid after contacting the substrate (i.e., tablets) in order to spread, provide even distribution, and coalesce into a unified film. The result is uniformity in coating layer coverage, thickness and composition homogeneity. If the coating liquid contains an insufficiently low level of solids, then a protracted drying phase may result. Consequently, the process time may be unfavorably long, with an increased likelihood for coated substrate agglomeration. In addition, an ideal coating facilitates the use of elevated drying temperatures to reduce process time.

More than anything, the ideal coating delivers superior product performance. Multiple properties characterize the final coating, including good coating adhesion and gloss, low surface roughness, good visual uniformity, good color intensity and color uniformity, good coating stability, and excellent logo (i.e., intagliations) sharpness. While the substrate to which the coating is applied can influence these properties, an ideal coating provides sufficient robustness to enable its extensive use on a variety of substrates. Additionally, the coated product does not exhibit moisture migration between the core and coating layer(s), which can alter product stability and release profiles.

Disclosures of pharmaceutically-acceptable coatings have been made in the prior art, and include: U.S. Pat. Nos. 4,576,604; 4,717,569; 5,273,760; 5,286,493; 5,407,686; 5,470,581; 5,630,871; 5,743,947; 5,998,478; 6,468,561; and 6,723,348. Nonetheless, the compositions and attributes of these coatings do not attain the qualities of the current invention.

For example, a trade brochure by International Specialty Products introduces hydroxypropylmethyl cellulose (HPMC) and poly(vinylpyrrolidone-co-vinyl acetate) (PVP/VA) coatings as an improvement over coatings containing only cellulose ethers, like HPMC. The HPMC-PVP/VA coatings exhibit low viscosity, and thus facilitate high coating production throughput. At 25% total solids level, the viscosity of a coating containing 90% PVP/VA and 10% HPMC (w/w) is about 9,500 cP lower than a 100% HPMC coating. In this brochure the HPMC-PVP/VA coating examples lack plasticizer, the addition of which is necessitated for coating flexibility ("robustness"). When added to a coating, PVP/VA and plasticizers can negatively impact the color stability of added colorants, a serious disadvantage for commercial products. The present invention overcomes this color stability limitation and additionally achieves smoother tablets than can otherwise be attained.

Also known in the prior art are coatings based on polydextrose, including coatings taught in U.S. Pat. No. 6,468,561. The addition of polydextrose resolves the color stability problem noted above for coatings containing only HPMC and PVP/VA. However, the HPMC-polydextrose coatings suffer a processability limitation due their viscosity when sprayed at the solids content levels expressed in the current invention. Compositions of the '561 patent have a high viscosity, especially for coatings containing 20% solids or more for which viscosities of 600 cP or more were reported. High viscosity is a major concern due to improper pumping and atomization of the coating. Therefore, high-throughput commercial applications are limited for the coatings taught by the '561 patent. The '561 patent also fails to disclose combined process and quality advantages achieved by the present invention, such as tablet smoothness, logo sharpness, and coating uniformity.

A PVP/VA barrier subcoat was reported by Gil et al., (*Eur. J. Pharm. Biopharm.*, 69, 1, 303-331, 2008) to serve as "a barrier to water penetration" in a controlled-release formulation of propranolol hydrochloride. The article reports that prototype tablets coated with the PVP/VA basecoat provided a sustained release of the active, which is inherently different from the immediate-release coating of the present invention. Also, surface quality attributes like smoothness and gloss, which are enhanced by compositions of the present invention, are of no or minor importance for a barrier subcoat layer described by Gil et al.

U.S. Pat. No. 6,723,348 teaches a taste-masking coating, which may comprise PVP/VA, specifically for the preparation of fexofenadine hydrochloride in the form of an orodispersible tablet. The disclosure does not include information on gloss, smoothness, color stability, or processing attributes, and does not disclose a film coating, as a continuum, applied completely across the surface of the finished dosage form.

Other examples of prior art teach PVP/VA-based coatings, but within a more narrow scope. For example, HPMC-PVP/VA coatings are taught in US patent application 2005/0112195 that comprise a high (85%-97% w/w) drug load. The polymers of such a coating are acknowledged in the patent application to help solubilize the high drug level. The application is silent on other product attributes like smoothness, gloss, and adhesion. In addition, the polymer content of the coating disclosed in the high-drug load application is very low, indicating that the true intent of the polymer is to act as a binder/suspending agent, and not as the primary film former that would allow an elegant film coating to be disposed onto the surface of a finished dosage form.

Additionally, coating compositions are described in other work, but lack reference of PVP/VA, including: aqueous maltodextrin-based coatings of U.S. Pat. No. 5,470,581; and cellulosic polymer-lactose coating taught in U.S. Pat. Nos. 5,630,871 and 5,743,947. They do not disclose the use or benefits of the PVP/VA copolymer.

In summary, the prior art provides a description of related water-based coatings, but none with the combined functionality of those described herein. Despite advances in coating materials and methods, there still exists a need for coatings that offer excellent processability (as described by coating viscosity and high solids content), good coating adhesion, improved color stability, and provide a smooth, uniform coated surface without negatively affecting drug release from the dosage form. The objective of the present invention is to disclose a novel coating composition that addresses each of these needs.

SUMMARY OF THE INVENTION

Water-based coatings have been discovered that resolve deficiencies noted in the prior art. These coatings comprise poly(N-vinyl-2-pyrrolidone-co-vinyl acetate) copolymer, a water-soluble cellulose ether, a film-forming agent based on D-glucose chemistry, and a plasticizer. Such compositions were previously unknown and provide across-the-board improvements in coating adhesion, smoothness, and color stability, as well as processability. Such compositions are directed for use in coating solid or solid-like substrates, especially those substrates in the agricultural, nutritional, pharmaceutical, and veterinary arts.

DETAILED DESCRIPTION OF THE INVENTION

Figure 1:
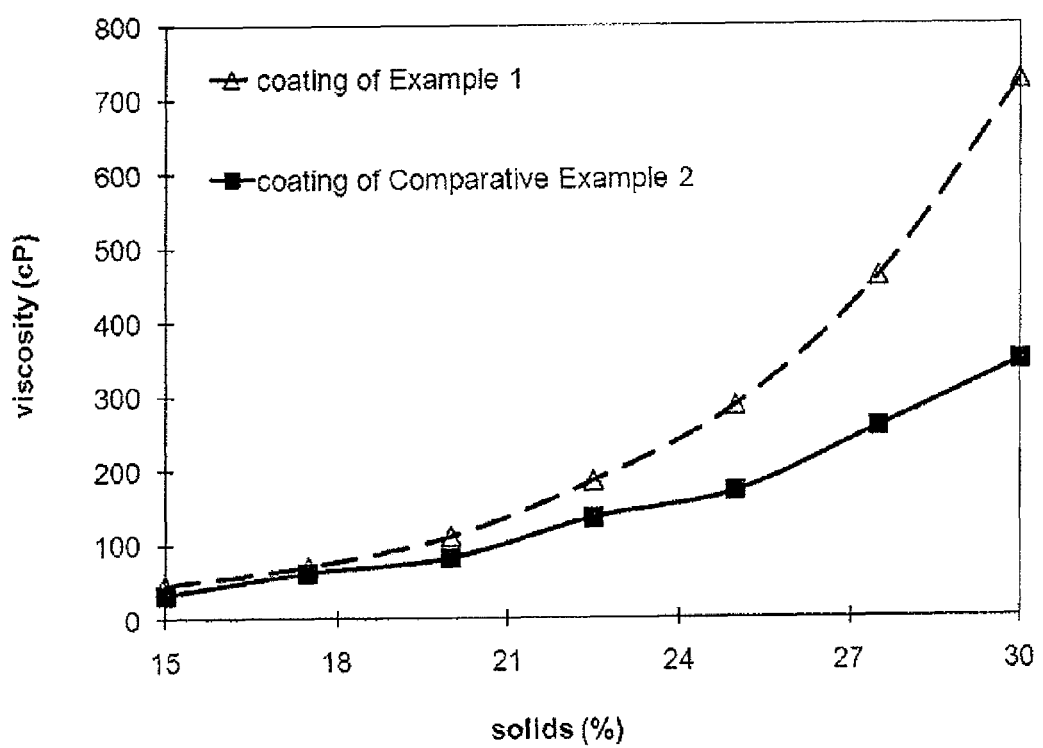
FIG. 1 is a graph of viscosity as a function of coating solids for the coatings produced in accordance with Comparative Example 2.
Figure 2A:
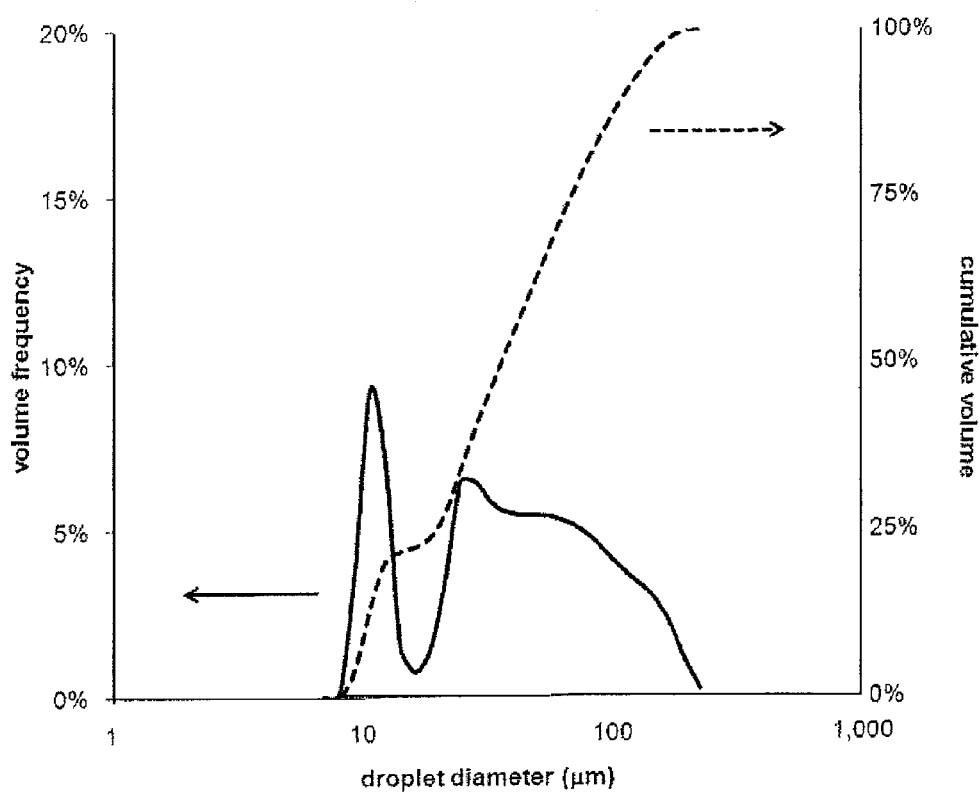
FIG. 2A-D are graphs of cumulative volume and weight fraction as a function of droplet diameter for the coating produced in accordance with Comparative Example 2.
Figure 2B:
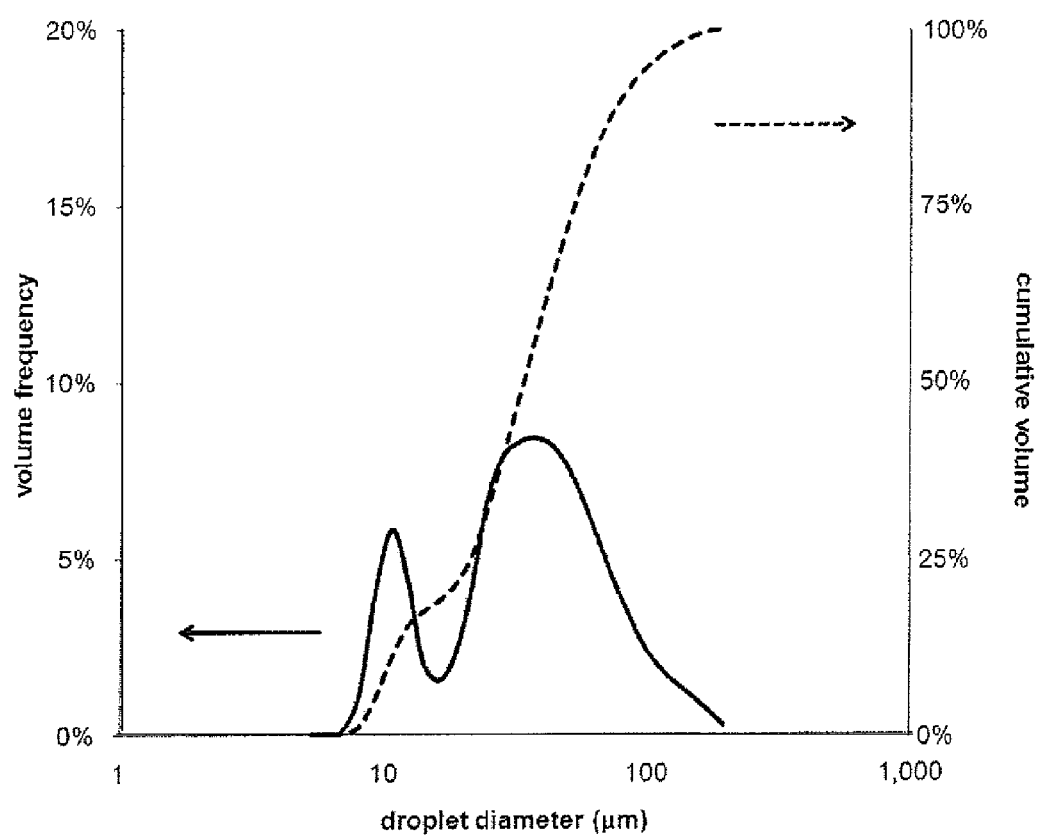
Figure 2C:
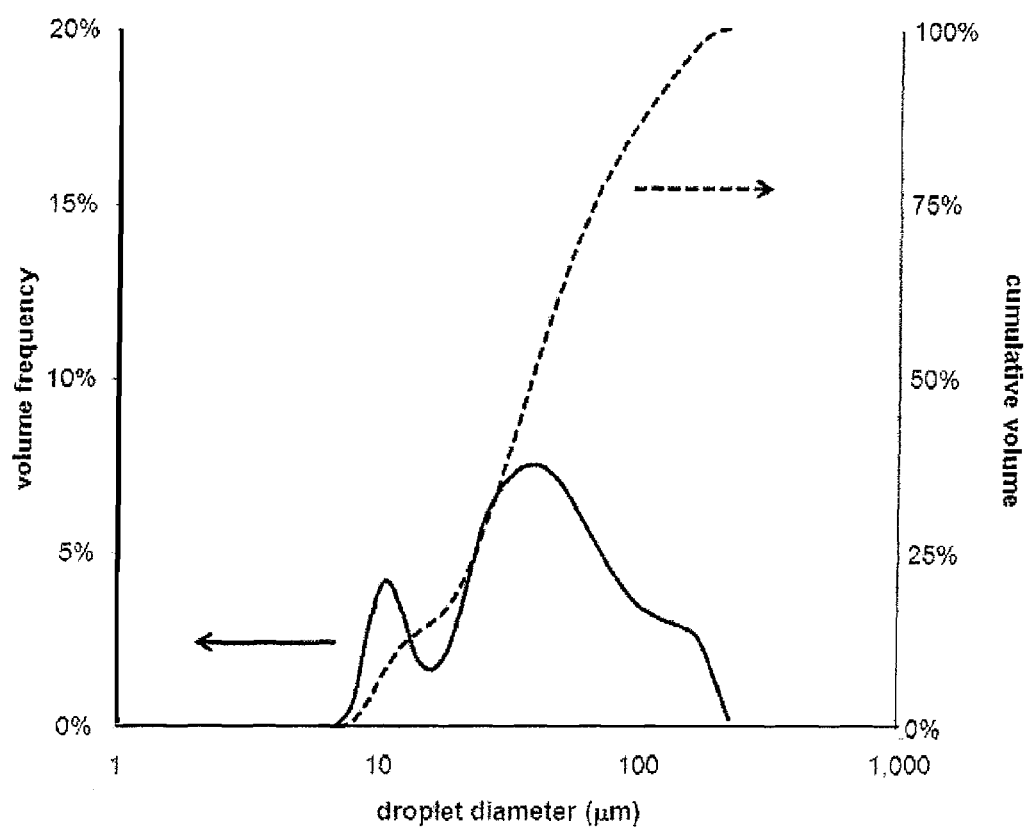
Figure 2D:
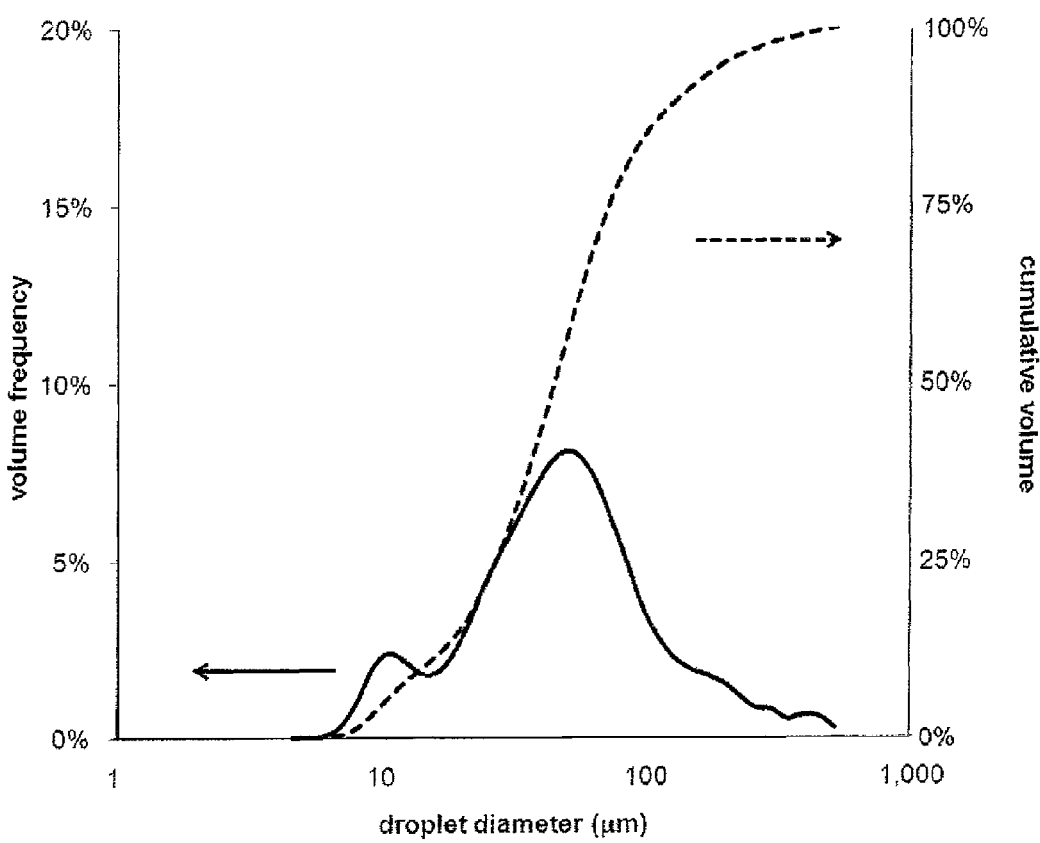
Figure 3A:
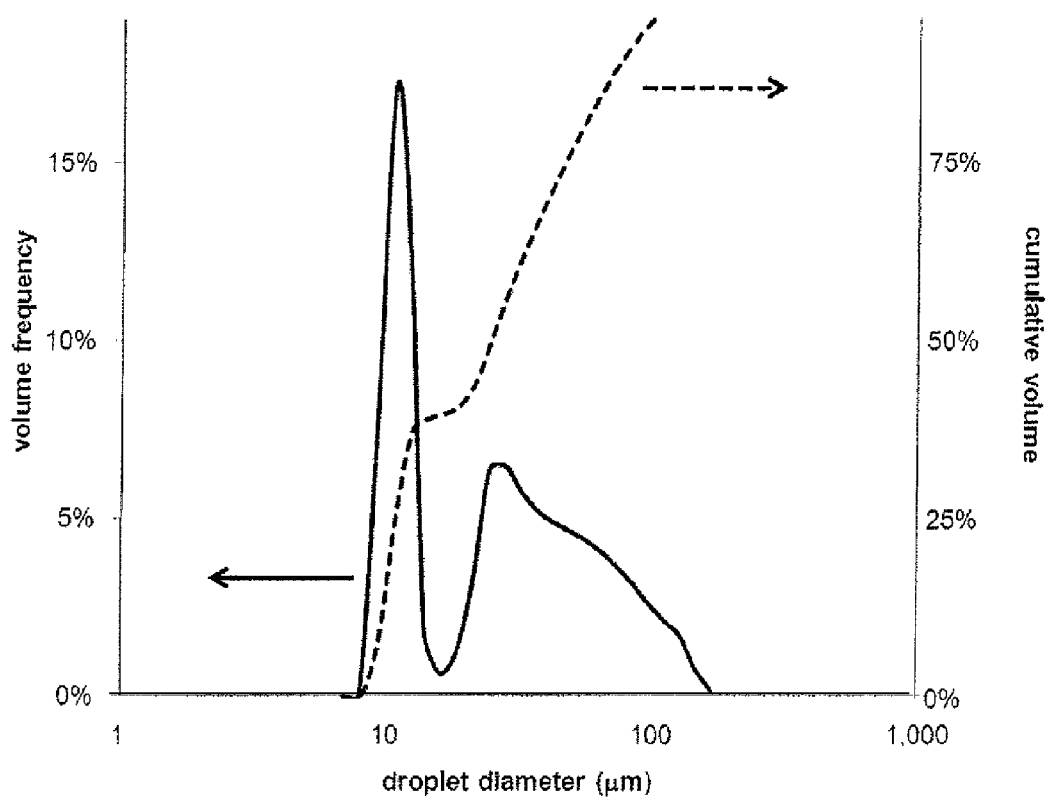
FIG. 3A-D are graphs of cumulative volume and weight fraction as a function of droplet diameter for the coating produced in accordance with Comparative Example 2.
Figure 3B:
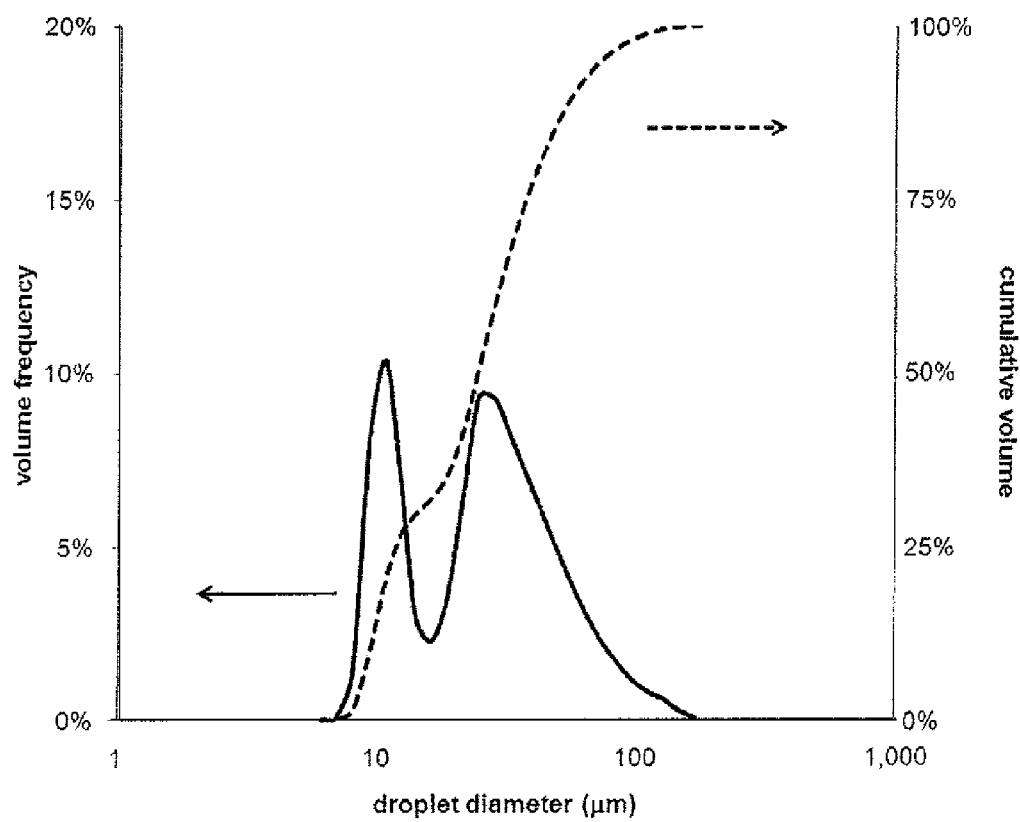
Figure 3C:
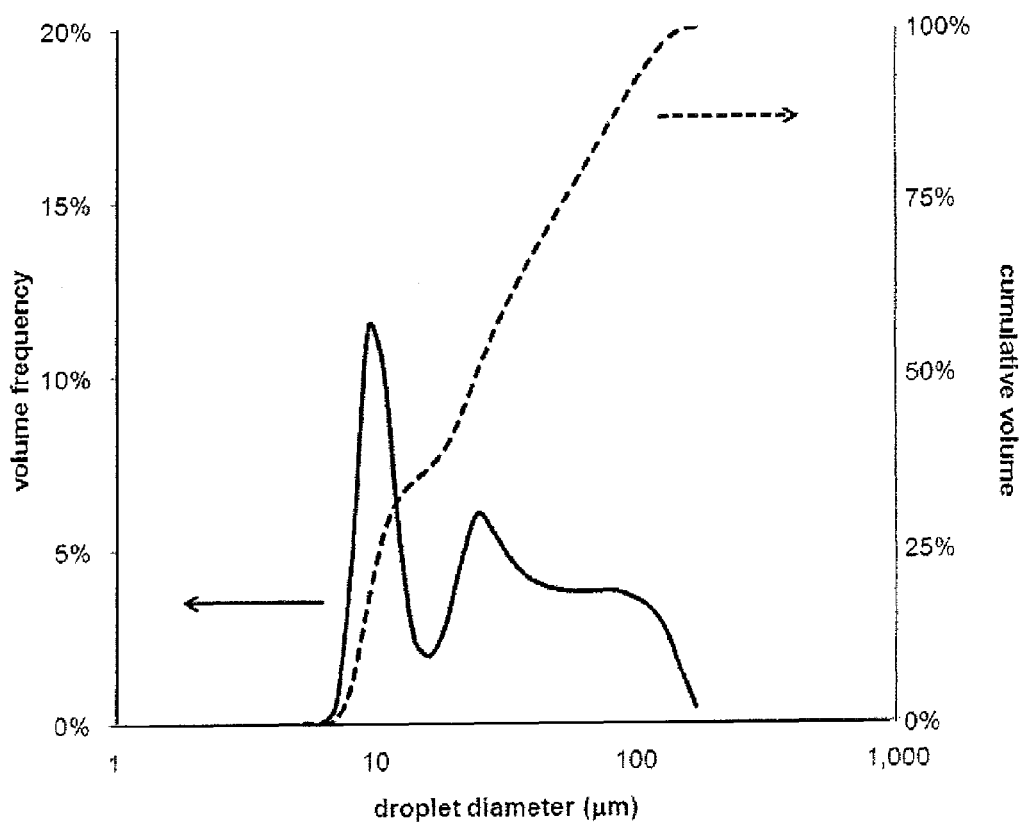
Figure 3D:
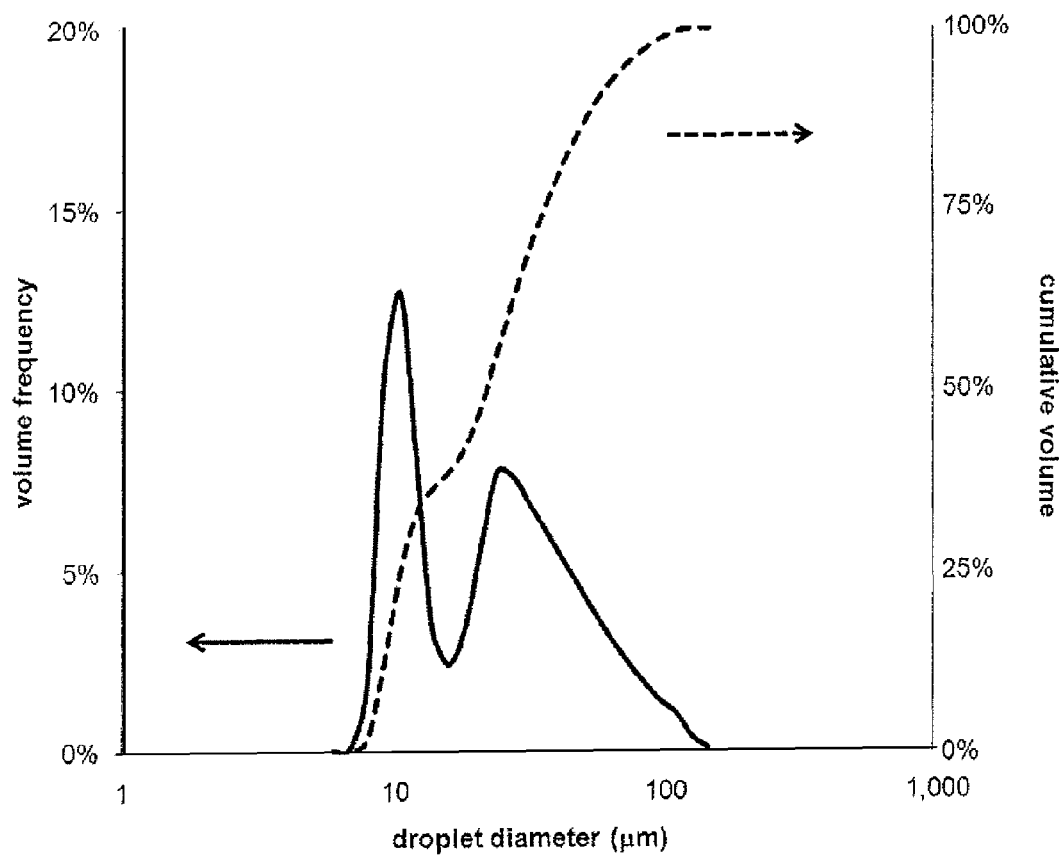

The term "comprising" encompasses the more restrictive terms "consisting essentially of" and "consisting of."

All percentages, ratio, and proportions used herein are based on a weight basis unless other specified.

The current invention describes water-based coatings and their coated products that provide an exceptional combination of properties not found in the prior art. The coatings are based on blends comprising poly(N-vinyl-2-pyrrolidone-co-vinyl acetate) copolymer, a water-soluble cellulose ether, a film-former based on D-glucose, and a plasticizer; the coating may optionally contain ingredients that may serve a role of colorants, such as dyes, pigments, and lakes. These coatings provide attributes that encompass improved coating adhesion, smoother tablets, enhanced color stability, and better processability than known coating compositions.

Poly(N-vinyl-2-pyrrolidone-co-vinyl acetate) copolymer

Poly(N-vinyl-2-pyrrolidone-co-vinyl acetate) (PVP/VA) copolymer possesses the general structure shown in formula:

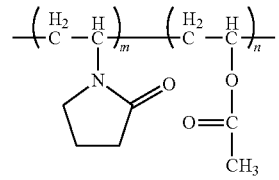

wherein m and n assume any integer equal to or greater than 1, and the PVP/VA copolymer is a random, linear copolymerization of the two monomers, N-vinyl-2-pyrrolidone and vinyl acetate. The copolymer containing the specific ratio of 60% N-vinyl-2-pyrrolidone and 40% vinyl acetate is also known as copovidone. Commercially manufactured PVP/VA copolymer includes Plasdone® S-630 by International Specialty Products, and Kollidon® VA64 by BASF, both of which contain the ratio 60% N-vinyl-2-pyrrolidone:40% vinyl acetate. A preferred method for measuring the molecular weight distribution of PVP/VA copolymer is gel permeation chromatograph employing multi-angle light scattering detection. The weight average molecular weight ($M_w$) of PVP/VA copolymer as measured by this method is about 35,000-65,000 atomic mass units (amu).

Increasing content of the vinyl acetate monomer (increasing values of n) has the result of decreasing the glass transition temperature and the water-solubility of the PVP/VA copolymer. To impart water-solubility, PVP/VA copolymers containing more than about 50% N-vinyl-2-pyrrolidone are preferred for use in this invention. Without restriction, typical monomer ratios range from about 55% N-vinyl-2-pyrrolidone:45% vinyl acetate to about 99% N-vinyl-2-pyrrolidone:1% vinyl acetate, and more preferably range from about 55% N-vinyl-2-pyrrolidone:45% vinyl acetate to about 75% N-vinyl-2-pyrrolidone:25% vinyl acetate. In an especially preferred embodiment, the copolymer contain a ratio of about 60% N-vinyl-2-pyrrolidone:40% vinyl acetate.

Cellulose Ethers

In addition to poly(N-vinyl-2-pyrrolidone-co-vinyl acetate) polymer, coatings of the invention also comprise at least one cellulose ether. Cellulose ethers are semi-synthetic derivatives of cellulose which are produced by substitution reactions of the 2-, 3-, and/or 5-hydroxyl groups of the D-glucose ring. As such, a general structure of water-soluble cellulose ethers that find application in the coating compositions described herein is:

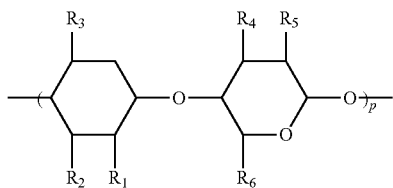

wherein each of $R_1$, $R_2$, $R_3$, $R_4$, $R_5$, and $R_6$ is independently selected. Examples of cellulose ethers that provide film-forming functionality include: carboxymethylcellulose sodium (CMC Na), hydroxyethyl cellulose (HEC), hydroxypropyl cellulose (HPC), hydroxypropylmethyl cellulose (HPMC), and methylcellulose (MC). These cellulose ethers differ in terms of the various R functional groups, the degrees of hydroxyl group substitution, and molecular weight.

Carboxymethylcellulose sodium is a sodium salt of a polycarboxymethyl ether of cellulose, wherein $R_1$, $R_2$, $R_4$, and $R_5$ are OH; and $R_3$ and $R_6$ are $CH_2OCH_2COONa$. CMC Na is provided by the following manufacturer under the trade names: Hercules Inc. (Aqualon® and Blanose®).

Hydroxyethyl cellulose is a partially substituted poly(hydroxyethyl)ether of cellulose, wherein $R_1$, $R_2$, $R_4$, and $R_5$ are OH and/or $O(CH_2CH_2O)_xH$; and $R_3$ and $R_6$ are $CH_2OH$ or $CH_2O(CH_2CH_2O)_xH$, wherein the subscript x represents the number of hydroxyethyl monomer units. HEC is manufactured by: Hercules Inc. (Natrosol® G, HX, HHX, G, and M).

Hydroxypropyl cellulose is a partially substituted poly(hydroxypropyl)ether of cellulose, wherein $R_1$, $R_2$, $R_4$, and $R_5$ are OH and/or $O[CH_2CH(CH_3)O]_yH$; and $R_3$ and $R_6$ are $CH_2OH$ and/or $CH_2O[CH_2CH(CH_3)O]_yH$, where the subscript y represents the number of hydroxypropyl monomer units. HPC grades produced by Hercules Inc. include: Klucel® EF, OF, HF, JF, LF, and MF.

Hydroxypropylmethyl cellulose, also known by its acronym HPMC and pharmaceutical grades are also known by the generic chemical name hypromellose. HPMC is a partially O-methylated and O-(2-hydroxypropylated) cellulose, wherein $R_1$, $R_2$, $R_4$, and $R_5$ are OH, $OCH_3$, and/or $O[CH_3CH(OH)CH_2]_y$; and $R_3$ and $R_6$ are $CH_2OH$, $CH_2OCH_3$ and/or $CH_2O[CH_3CH(OH)CH_2]_y$, where the subscript y represents the number of hydroxypropyl monomer units. The following companies manufacture HPMC: Dow Chemical (Methocel™ grades E3, E5, E6, E15, E50, E4M, E10M, F50, K3, K100, K4M, K15M, K100M), Shin-Etsu Chemical Company (Pharmacoat grades 603, 606, 615, 904), and Hercules Inc. (Benecel® MP 843, 814, and 844).

Methylcellulose is the simplest substituted cellulose ether, wherein $R_1$, $R_2$, $R_4$, and $R_5$ are OH and/or $OCH_3$; and $R_3$ and $R_6$ are OH and/or $CH_2OCH_3$. Methylcellulose is commercially manufactured by the following companies: Dow Chemical Company (Methocel™ A4C, A4M, A15, and A15C); and Shin Etsu Chemical Company (Metolose SM).

Plasticizer

The plasticizer specified in the described invention is any of the known compositions that enhance the plastic properties of polymeric composition, for example, increasing flexibility and/or durability by lowering the glass transition temperature ($T_g$) of the composition. Preferably the plasticizer is approved for human use. Examples of such plasticizers include (in alphabetical order): citrates (e.g., acetyltributyl, acetyltriethyl, tributyl, and triethyl citrates), glycols (e.g., polyethylene glycol and propylene glycol, glycerin), medium-chain triglycerides (e.g., mixtures of caprylic acid and capric acid), phthalates (e.g., dibutyl, diethyl, and dimethyl phthalates), stearates (e.g., glyceryl monostearate), and triacetin. The necessary plasticizer addition level is dependent on the grades of HPMC and copovidone, and thus the degree of plasticization needed.

D-Glucose Film-Forming Agent

The invented coatings also comprise a film-forming agent based on D-glucose chemistry selected from the group consisting of lactose, maltodextrin, maltose, polydextrose, starch, and trehalose. These materials all share a common chemistry as suggested by the formula:

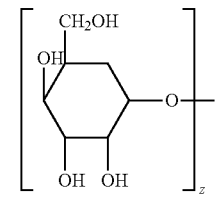

wherein z represents the number of D-glucose units. Especially preferred D-glucose film-forming agents include maltodextrin and polydextrose.

Maltodextrin is a water-soluble polysaccharide with an empirical formula of $(C_6H_{10}O_5)_z \cdot H_2O$. It is composed of 1-4 and 1-6 glycosidic linkages of the D-glucose unit. Commercially-available examples of maltodextrin include the Maltrin® M040, M100, M150, M180, M510, M520, and M700 products by Grain Processing Corporation.

Polydextrose, also known as poly-D-glucose, is a synthetic, water-soluble, highly cross-linked polymer of glucose with smaller amounts of sorbitol and citric acid. Polydextrose has an empirical formula of $(C_6H_{12}O_6)_z$. The 1,4-glycosidic linkages predominate in polydextrose, but other linkages naturally occur. Relative to other polymers, polydextrose may be considered a low molecular weight polymer, since the range in molecular weight is about 500 amu-20,000 amu. Descriptions of polydextrose are provided in monographs of the *US Pharmacopeia* 31/*National Formulary* 26 (US Pharmacopeia, Rockville, Md., 2007) and the *Food Chemical Codex, Sixth Edition* (US Pharmacopeia, Rockville, Md., 2008), both of which are incorporated in their entirety by reference. Commercially available polydextrose is available from a number of manufacturers and trade names, including: Danisco Sweeteners Ltd. (Litesse®, Litesse® Two, and Litesse® Ultra).

Copovidone, HPMC, the exemplified film-forming agents based on D-glucose, and the exemplified plasticizers are described in *The Handbook of Pharmaceutical Excipients* by R. C. Rowe, P. J. Sheskey, and S. C. Owen (Pharmaceutical Press and American Pharmaceutical Association, 2003), which is incorporated in its entirety by reference.

Composition Levels

The addition levels for these four ingredients are only limited inasmuch as to ensure adequate coating preparation, process application, and final properties. For example, the PVP/VA copolymer addition levels are dependent on the ratio of N-vinyl-2-pyrrolidone:vinyl acetate. If the PVP/VA copolymer that contain 60% N-vinyl-2-pyrrolidone: 40% vinyl acetate is used, then the coating should not contain more than 45% PVP/VA copolymer in order to avoid coatings that are too tacky to be handled. Likewise, a minimum level of the cellulose ether is required in order to create robust films, while the upper addition level is constrained only to the extent that high solids coatings (i.e., more than 20%) remain processable (i.e., without pumping or atomization defects). Finally, the plasticizer content in the coating should be sufficient to plasticize the dry film (meaning it is flexible enough to avoid chipping and cracking during the coating, drying, and handling process), yet still produce a dry, free-flowing powder that does not coalesce.

Coatings of the present invention exhibit the desired properties when they comprise:
    about 25% to 66% water-soluble cellulose ether,
    about 0.5% to 60% PVP/VA copolymer,
    about 0.1% to 45% film-forming agent based on D-glucose, and
    about 6% to 22% plasticizer.

More preferably the non-pigmented coating compositions comprise:
    about 30% to 50% water-soluble cellulose ether,
    about 25% to 45% PVP/VA copolymer,
    about 6% to 37% film-forming agent based on D-glucose, and
    about 8% to 22% plasticizer.

In especially preferred, non-pigmented embodiments the coating compositions comprise:
    about 30% to 35% water-soluble cellulose ether,
    about 30% to 35% PVP/VA copolymer,
    about 20% to 25% film-forming agent based on D-glucose, and
    about 15% to 20% plasticizer.

When an ingredient that can serve the role of a colorant (which include, but are not limited to pigments, lakes, and dyes), is incorporated into a coating, the levels defined above change. Accordingly, colorant-containing coatings of the present invention exhibit desired properties when they comprise:
    about 20% to 45% water-soluble cellulose ether,
    about 0.5% to 40% PVP/VA copolymer,
    about 0.1% to 30% film-forming agent based on D-glucose,
    about 5% to 15% plasticizer, and
    up to about 30% colorant.

More preferably the colorant-containing coating compositions comprise:
    about 25% to 35% water-soluble cellulose ether,
    about 20% to 30% PVP/VA copolymer,
    about 5% to 25% film-forming agent based on D-glucose,
    about 7% to 15% plasticizer, and
    up to about 30% colorant.

In especially preferred embodiments the colorant-containing coating compositions comprise:
    about 25% to 30% water-soluble cellulose ether,
    about 20% to 25% PVP/VA copolymer,
    about 10% to 20% film-forming agent based on D-glucose,
    about 7% to 13% plasticizer, and
    up to about 30% colorant.

Methods for manufacturing these coating systems as dry powders are known to one skilled in the art, and include dry blending ingredients using commercial-grade mixers, including high-shear mixers of the design manufactured by Littleford Day, Inc. If it is advantageous to use liquid ingredients, such as triethyl citrate as plasticizer, then they may be sprayed into and during the dry blending of the powdered materials.

Methods of applying the water-based film coating are generally those known to one skilled in the art, and include the application of the liquid coating, using a spray-atomization technique, in either a fluid-bed coater (top-spray, bottom spray, or tangential spray) or a pan coater (solid wall and partially perforated or fully perforated side-vented coating pans); film coating is a common embodiment of each and every one of these techniques. Examples of commercial manufacturers of suitable coating equipment and their models include: O'Hara Technologies (Labcoat M/MX Tablet Coating System; Labcoat I, II-X, and III; and Fastcoat), Manesty (Premier 200), GEA Process Engineering Inc. (Precision Coater™, Top Spray Coater™, Niro Pharma Spray Dryer™), and Cronimo Group (Multi Cota).

It has been discovered that the aforementioned coating compositions produce surprisingly robust coatings that can be processed much more aggressively than would normally be expected by those with ordinary skill in the art, especially when compared to other types of coatings. The benefits of these coating compositions are provided in the examples (as indicated in FIGS. 1, 2 and 3).

EXAMPLES

Example 1

A coating formula of this invention was developed and contained the ingredients shown in Table 1. This coating was made at up to 25% total solids and contained HPMC, copovidone, polydextrose, polyethylene glycol, and a medium-chain triglyceride, which is sold under the trade name of Miglyol®. In this case, Miglyol® and polyethylene glycol function as plasticizers, with the primary purpose of increasing film flexibility.

This coating was applied onto 2 kg of uncoated tablets using a laboratory-scale coater, the O'Hara Labcoat II-X fitted with a 15-inch pan. The operating conditions used to produce the reference coated tablets are summarized in Table 2.

The robustness of this coating enabled process scale-up from laboratory- to pilot-scale equipment and finally to production-scale equipment (Table 2).

TABLE 1

Coating formula of Example 1

| Ingredient | | Dry-Basis Addition Level (w/w) |
|---|---|---|
| HPMC | type 2910, 6 cP | 25.0% |
| copovidone | Plasdone ® S-630 | 22.5% |
| polyethylene glycol | type 3350 | 9.5% |
| polydextrose | Litesse ® Two | 15.0% |
| medium-chain triglycerides | Miglyol ® 810 | 3.0% |
| pigment | | 25.0% |
| total | | 100.0% |

TABLE 2

Process conditions to create coated tablets according to Example 1

| | parameter settings | | |
|---|---|---|---|
| process parameter | laboratory scale | pilot scale | production scale |
| Equipment Characteristics | | | |
| pan type | O'Hara LabCoat II-X fitted with 15-inch pan | O'Hara LabCoat II-X fitted with 30-inch pan | Manesty Premier 200 |
| spray gun type | Schlick fitted with ABC nozzle | Schlick fitted with ABC nozzles | Manesty Opticoat |
| number of spray guns used | 1 | 2 | 3 |
| Specific Process Conditions Used | | | |
| pan loading (kg) | 2 | 40 | 170 |
| gun-to-bed distance (cm) | 16 | 19 | 25-28 |
| pan speed (rpm) | 15-20 | 7-10 | 6-8 |
| process air volume (m³/h) | 250 | 600-700 | 2300-2500 |
| inlet air dew point (° C.) | 10-13 | 10-13 | 10-13 |
| inlet air temperature (° C.) | 55-60 | 55-60 | 60-65 |
| tablet bed temperature (° C.) | 42-48 | 38-44 | 38-42 |
| exhaust air temperature (° C.) | 45-48 | 35-40 | 45-50 |
| atomizing air pressure (bar) | 1.0-1.5 | 1.0-2.0 | 1.5-3.0 |
| pattern air pressure (bar) | 2.0-3.0 | 2.0-3.0 | 2.0-3.5 |
| coating solids (% w/w in water) | 20-25 | 20-25 | 20-25 |
| spray rate (g/min) | 15-15.5 | 95-100 | 380-420 |

Comparative Example 1

A comparative coating was made to 19% total solids by dissolving HPMC, a strong film former, with copovidone, which considerably weakens film strength (Table 3). As this comparative coating contains no polydextrose and has a higher overall level of HPMC, it would be considered by one with ordinary skill in the art to be more robust than the formulation of Example 1 (shown in Table 1)

This coating was applied to 2 kg of the same lot of uncoated tablets of Example 1. The same process equipment of Example 1 was employed and the conditions are summarized in Table 4.

In order to obtain acceptable coated tablets, a very gentle coating process condition was required for this coating. The coating pan rotational speed was 12 revolutions per minute (rpm), instead of the more typical 18 rpm-20 rpm for the particular pan used. Attempts to increase the pan rotational speed resulted in worn tablet edges. Additionally, an increase in coatings solids level could not be made without adversely affecting coated tablet quality. As a result, the coating of this comparative example was deemed unsuitable and was not selected for scale-up to larger size equipment.

TABLE 3

Coating formula of Comparative Example 1

| ingredient | dry-basis addition level (w/w) |
|---|---|
| HPMC (grade 2910, 6 cP) | 47.0% |
| copovidone (60% VP/40% VA ratio) | 15.5% |
| polyethylene glycol 3350 | 12.5% |
| pigment | 25.0% |
| total | 100.0% |
| coating solids content in water | 19.0% |

TABLE 4

Process conditions to create the coated tablets of Comparative Example 1

| process parameter | setting |
|---|---|
| pan type | O'Hara LabCoat II-X fitted with 15-inch pan |
| spray gun type | Schlick fitted with ABC nozzle |
| number of spray guns used | 1 |

TABLE 4-continued

Process conditions to create the coated tablets of Comparative Example 1

| process parameter | setting |
|---|---|
| pan loading (kg) | 2 |
| gun-to-bed distance (cm) | 8 |
| pan speed (rpm) | 12 |
| process air volume (m³/h) | 250 |
| inlet air dew point (° C.) | 10-13 |
| inlet air temperature (° C.) | 55-60 |
| tablet bed temperature (° C.) | 42-48 |
| exhaust air temperature (° C.) | 45-48 |
| atomizing air pressure (bar) | 1.0-1.5 |
| pattern air pressure (bar) | 2.0-3.0 |
| coating solids (% w/w) | 20-25 |
| spray rate (g/min) | 15-15.5 |

Comparative Example 2

The coating of Example 1 was compared to a commercially available poly(vinyl alcohol) (PVA)-based coating (Opadry® II, BPSI Holdings). Suspensions of each coating were prepared at the following total solids in water: 15%, 17.5%, 20%, 22.5%, 25%, 27.5% and 30%.

The viscosities of the these suspensions were measured using a TA Instruments ARG2 Rheometer fitted with 60 mm stainless steel parallel plates. The viscosities were measured at room (22° C.) temperature.

The coating from Example 1 consistently produced higher viscosities than the coating of Comparative Example 2 (FIG. 1).

The atomization characteristics of the coating of Example 1 and the coating of Comparative Example 2 were examined using a Schlick ABC spray nozzle, and droplet sizes and size distributions were measured using a Malvern Laser Droplet Size Analyzer. Suspensions prepared at 20% and 25% solids in water for the coating of Example 1 and the coating of Comparative Example 2 were analyzed. Droplet size was examined 2 cm from the nozzle tip, and 12 cm from the nozzle tip, the latter distance is representative of the gun-to-bed distance typical of laboratory-scale coating pans. The spray rate used was 24 g/min, the atomizing air pressure was 1.0 bar, and the pattern air pressure 1.5 bar.

Table 5 summarizes the coating systems and measured suspension atomization data presented in FIG. 2A-D and FIG. 3A-D. Surprisingly, in spite of exhibiting higher suspension viscosities, the coating of Example 1 produces notably finer droplets on atomization, irrespective of whether the coating liquid was sprayed at either 20% or 25% solids. Both coating systems produce bi-modal droplet size distributions. However, in the case of the coating of Example 1, there is a greater contribution of the finer droplet distribution, while in the case of the coating of Comparative Example 2, the contribution from the coarser droplet distribution is more evident.

TABLE 5

Summary of coating systems and measured suspension atomization data of FIG. 2A-D and FIG. 3A-D

| | | coating | | | | |
|---|---|---|---|---|---|---|
| figure | ID | total solids | gun-to-bed distance (cm) | particle size distribution (μm) | | |
| | | | | $D_v10$ | $D_v50$ | $D_v90$ |
| 2A | Comparative Example 2 | 20% | 2 | 9.98 | 34.89 | 107.60 |
| 2B | Comparative Example 2 | 20% | 12 | 10.19 | 32.68 | 75.98 |
| 2C | Comparative Example 2 | 25% | 2 | 11.36 | 37.81 | 110.16 |
| 2D | Comparative Example 2 | 25% | 12 | 14.02 | 43.62 | 126.28 |
| 3A | Example 1 | 20% | 2 | 9.27 | 23.75 | 74.02 |
| 3B | Example 1 | 20% | 12 | 9.18 | 23.60 | 53.94 |
| 3C | Example 1 | 25% | 2 | 8.39 | 23.72 | 88.97 |
| 3D | Example 1 | 25% | 12 | 8.86 | 21.70 | 55.58 |

Comparative Example 3

The coating of Example 1 and the coating of Comparative Example 2 each were applied to 2 kg batches of uncoated, convex, round placebo tablets in a Vector LDCS coater fitted with a 2.5 L fully-perforated pan using process conditions outlined in Table 6.

TABLE 6

Coating process conditions used to create coated tablets according to Comparative Example 2

| parameter | value |
|---|---|
| fixed settings | |
| Spray nozzle diameter (mm) | 1.0 |
| Pan loading (kg) | 2.0 |
| Process air flow (m³/h) | 102 |
| Inlet temperature (° C.) | 60 |
| Pattern air pressure (bar) | 1.0 |
| Pan speed (rpm) | 22 |
| variable settings | |
| Coating solids (% w/w) | 15-25 |
| Spray rate (g/min) | 9-16 |
| Atomizing air pressure (bar) | 0.7-1.4 |

Figure 4A:
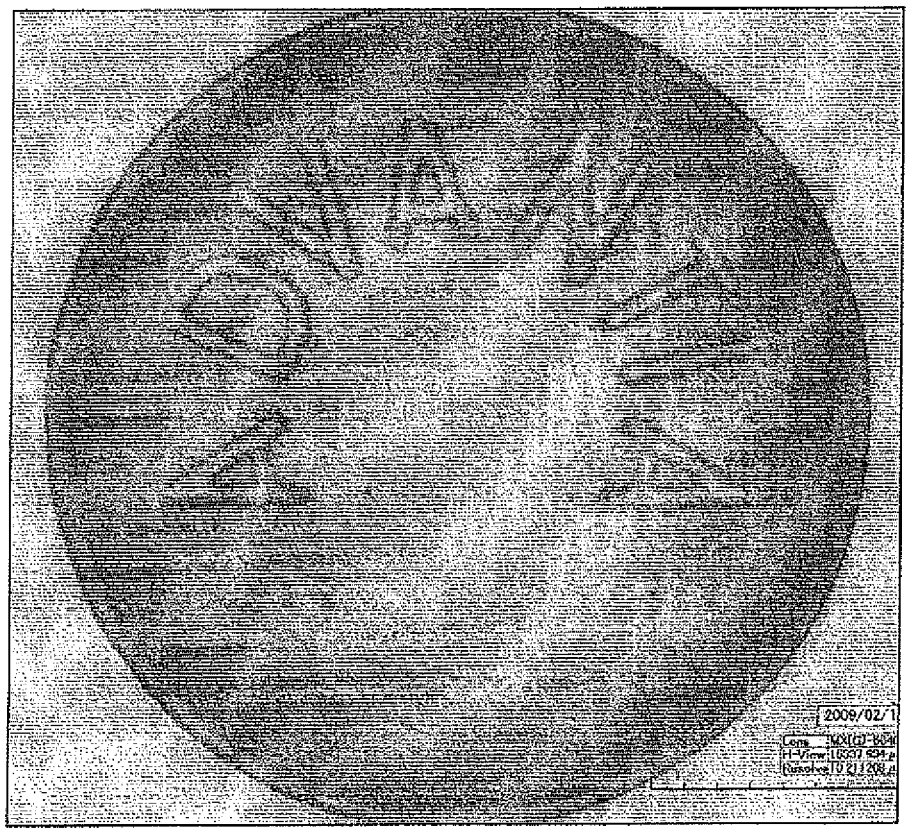
FIG. 4A-B are photographs of coated tablets produced in accordance with Comparative Example 3.
Figure 4B:
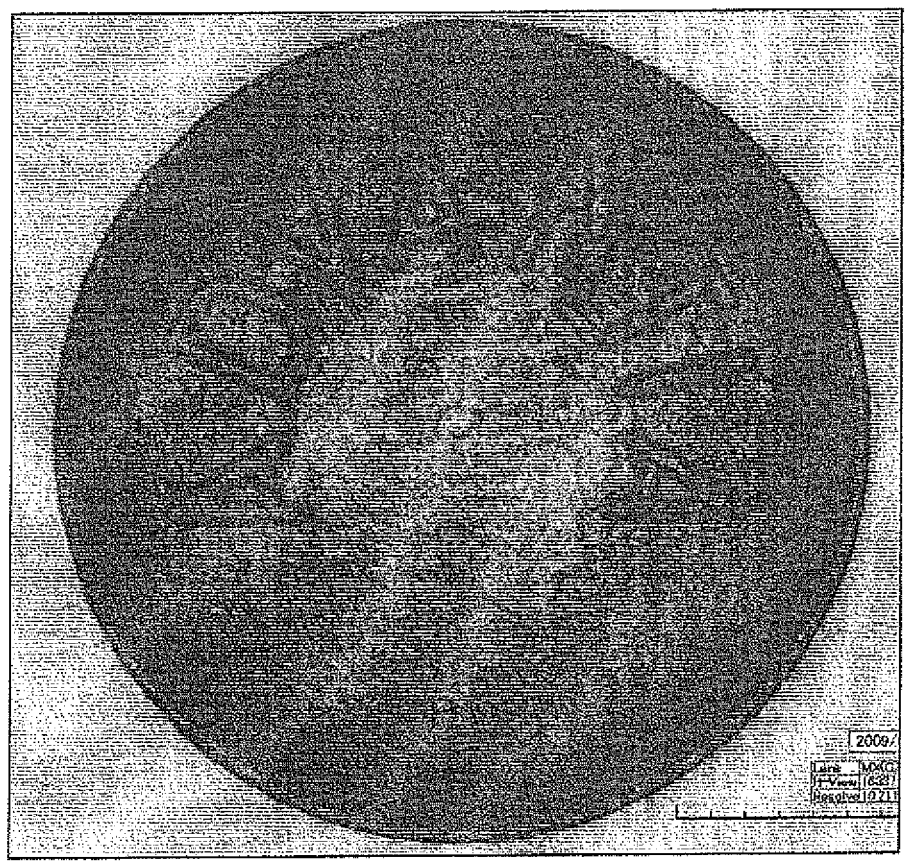
Figure 5A:
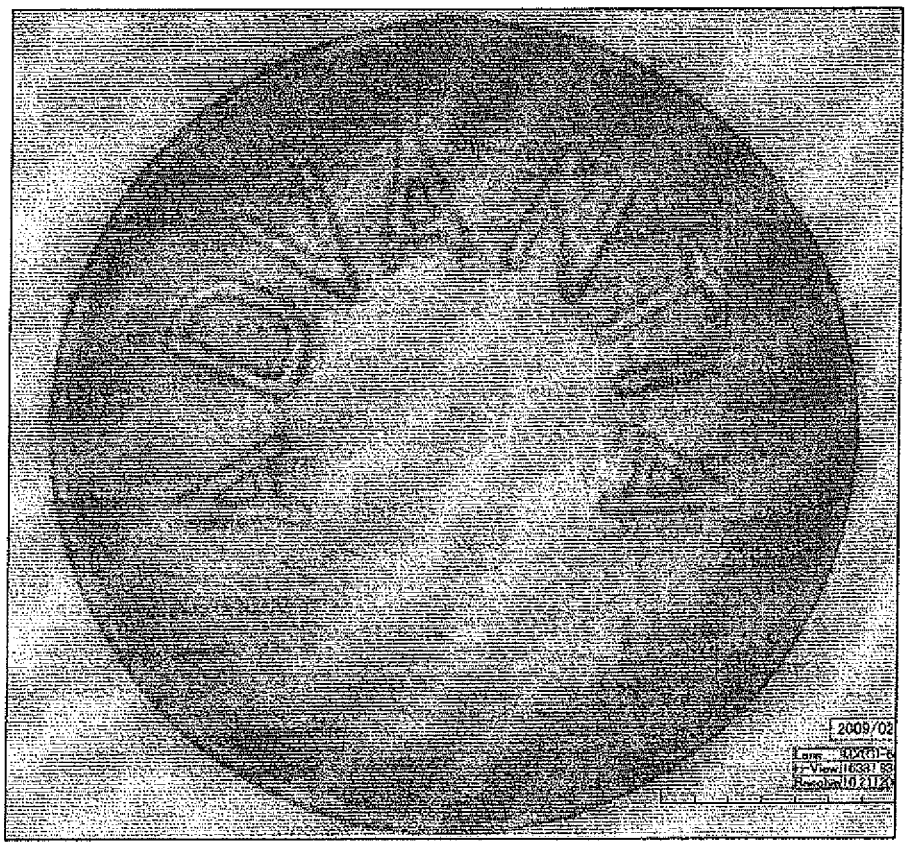
FIG. 5A-B are photographs of coated tablets produced in accordance with Comparative Example 3.
Figure 5B:

FIGS. 4A and 4B show tablets coated with the coating of Example 1 and the coating of Comparative Example 2, respectively, each applied at 15% solids with a spray rate of 9 g/min and atomization air pressure of 1.4 bar. FIG. 5A-B show tablets coated with the coating of Example 1 and the coating of Comparative Example 2, respectively, each applied at 20% solids with a spray rate of 12.5 g/min and atomization air pressure of 1.0 bar. In spite of its higher viscosity, a high-solids coating of this invention (Example 1) produced smoother and more uniform coated tablets than the coating of Comparative Example 2, as indicated in FIG. 4A-B and FIG. 5A-B by Hirox digital microscopy.

At the same time, tablets coated with the formula of Example 1 exhibit sharper and better defined intagliations than those of the coating from Comparative Example 2.

Figure 6:
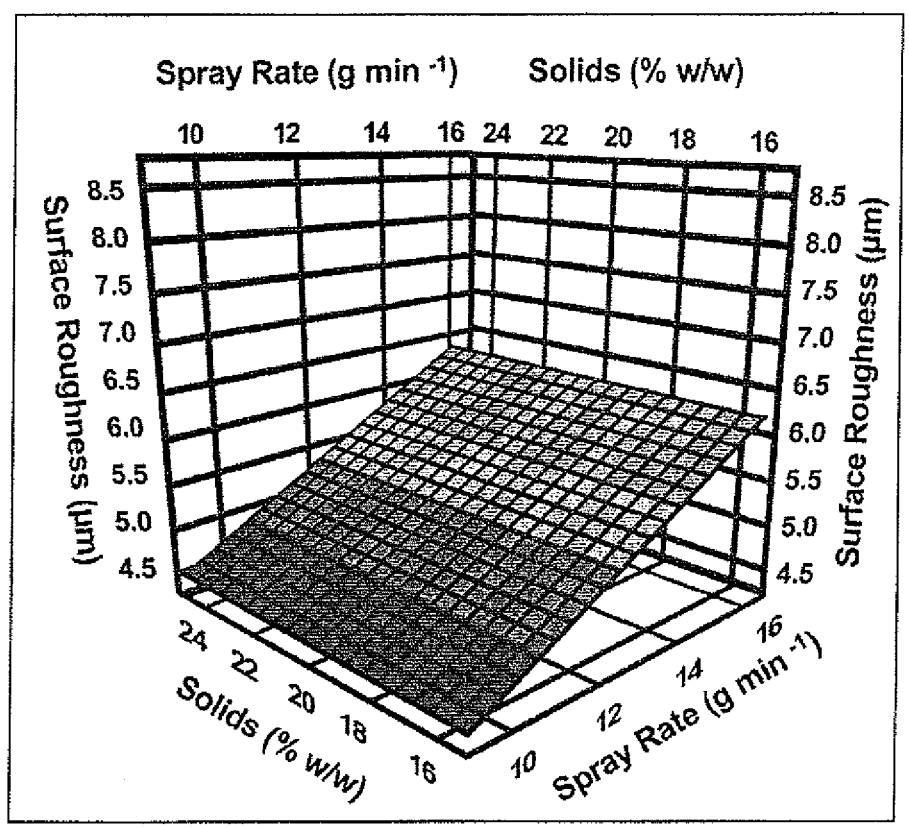
FIG. 6 is a graph of surface roughness as a function of spray rate and coating solids produced in accordance with Comparative Example 3.
Figure 7:
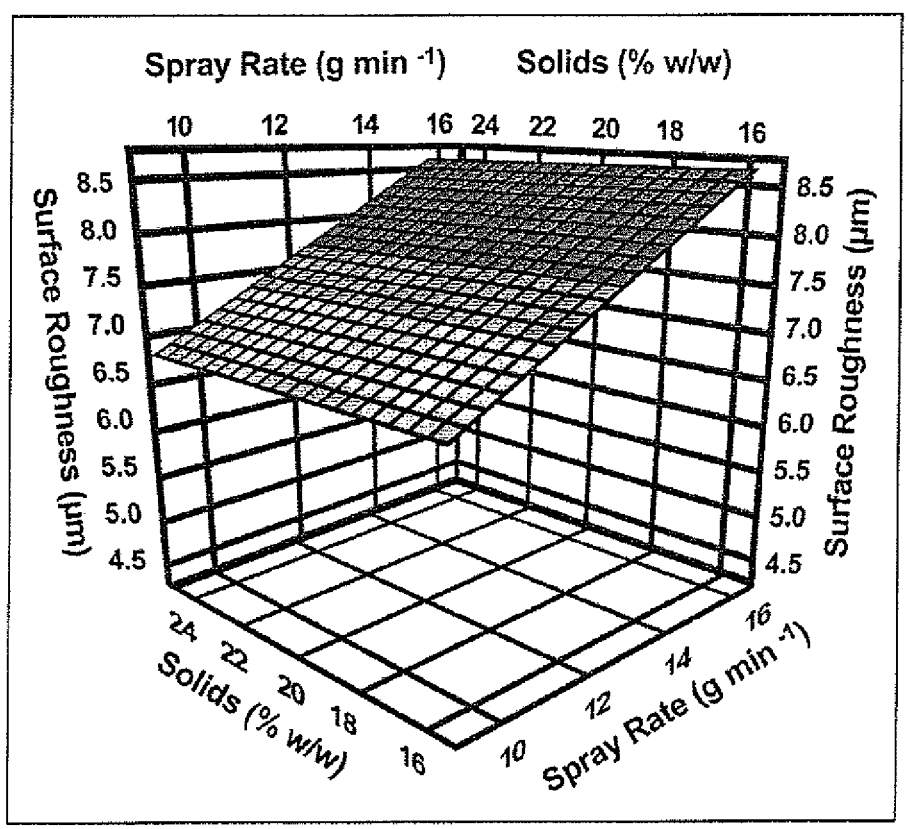
FIG. 7 is a graph of surface roughness as a function of spray rate and coating solids produced in accordance with Comparative Example 3.

The coated tablets of this example also were evaluated for coated surface roughness, as measured by light-scanning profilometry (Nanovea CHR 150, Microphotonics Inc.). FIG. 6 is the response surface graph for surface roughness for coated tablets of Example 1. FIG. 7 is the response surface graph for surface roughness for coated tablets of Comparative Example 2. The surface roughness values, Sq, for the tablets coated with the coating of Example 1 were consistently lower than the measured values for Comparative Example 2. These data indicate that the nature of the employed coating system had the greatest impact on roughness values obtained, followed by spray rate.

The results of this example are counterintuitive. The monograph by M. E. Aulton and A. M. Twitchell titled, "Film Coat Quality," chapter 13 in the book *Pharmaceutical Coating Technology* (G. Cole, et al., Informa Healthcare, 2007), which hereby is incorporated by reference, demonstrated that surface roughness increases as coating solids content and solution viscosity increase (Table 7). At 20% total solids the coating of Example 1 possessed a higher viscosity, yet gave smoother, more visually uniform tablets than the coating from Comparative Example 2 made to 15% and 20% total solids, both of which has a lower viscosity.

TABLE 7

Surface roughness as a function of coating solids content and solution viscosity (data of Aulton and Twitchell, ibid.)

| coating solids content | solution viscosity (cP) | surface roughness (µm) |
|---|---|---|
| 6% w/w | 45 | 1.83 |
| 9% w/w | 166 | 2.53 |
| 12% w/w | 520 | 3.51 |

Example 2

A coating formula of this invention was developed and contained the composition shown in Table 8. A suspension of this coating was made at 22.5% total solids in water.

TABLE 8

Coating formula of Example 2

| ingredient | | dry-basis addition level (w/w) |
|---|---|---|
| HPMC | type 2910, 6 cP | 25.00% |
| copovidone | Plasdone ® S-630 | 22.50% |
| polyethylene glycol | type 3350 | 9.50% |
| polydextrose | Litesse ® Two | 15.00% |
| medium-chain triglycerides | Miglyol ® 810 | 3.00% |
| titanium dioxide | | 24.41% |
| FD&C Blue No. 2 Lake (13%) | | 0.25% |
| FD&C Red No. 40 Lake (15%) | | 0.12% |
| FD&C Yellow No. 6 Lake (18%) | | 0.22% |
| total | | 100.00% |

The coating of Example 2 was applied to 2 kg of ibuprofen tablets using a Vector LDCS coater fitted with a 2.5 L fully-perforated pan. The coating process conditions used are shown in Table 9.

TABLE 9

Process conditions used for the coating application of Example 2

| parameter | value |
|---|---|
| Inlet temperature (° C.) | 60 |
| Exhaust temperature (° C.) | 38 |
| Spray rate (g/min) | 15 |
| Atomizing air pressure (bar) | 2 |
| Pattern air pressure (bar) | 2.3 |
| Spray nozzle diameter (mm) | 1.0 |
| Process air flow (m³/h) | 102 |
| Pan speed (rpm) | 20 |
| Coating solids (% w/w) | 22.5 |

Figure 8:
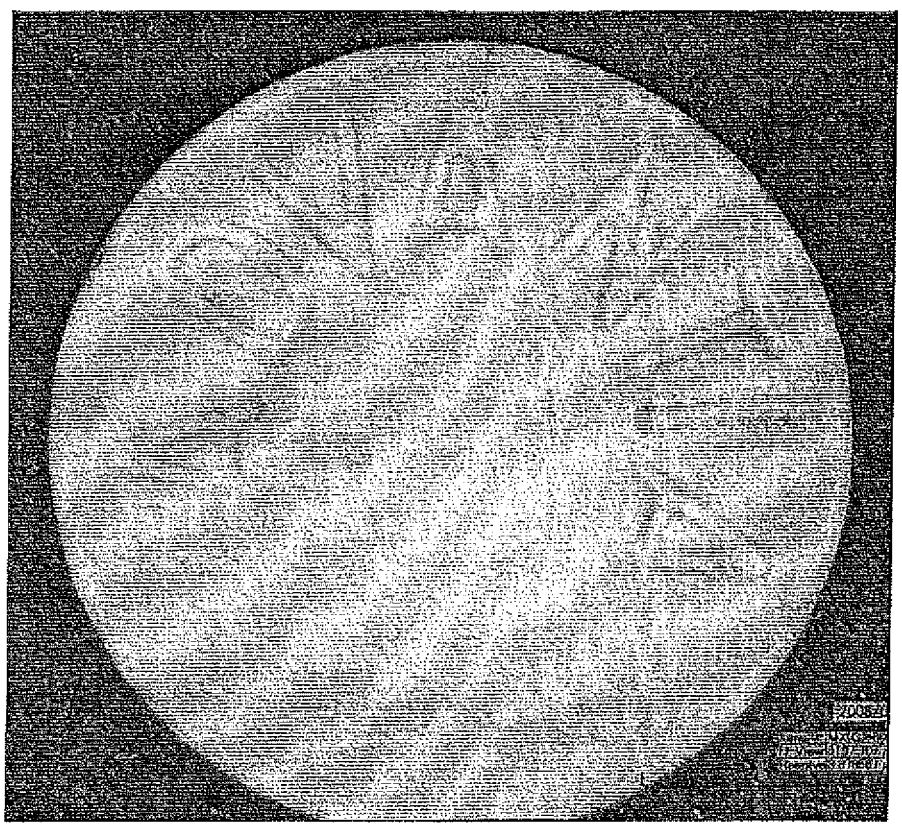
FIG. 8 is a photograph of a coated tablet produced in accordance with Example 2.

The coated tablets were uniformly colored, smooth and have excellent logo definition. FIG. 8 is a photomicrograph of one of the coated tablets of this Example.

Example 3

A coating formula of this invention was developed and contained the composition shown in Table 10. A suspension of this coating was made at 20% total solids in water.

TABLE 10

Coating formula of Example 3

| ingredient | | dry-basis addition level (w/w) |
|---|---|---|
| HPMC | type 2910, 6 cP | 25.0% |
| copovidone | Plasdone ® S-630 | 22.5% |
| polyethylene glycol | type 3350 | 9.5% |
| polydextrose | Litesse ® Two | 15.0% |
| medium-chain triglycerides | Miglyol ® 810 | 3.0% |
| titanium dioxide | | 25.0% |
| total | | 100.0% |

The coating of Example 3 was applied to 0.45 kg of multivitamin tablets using a Vector LDCS coater fitted with a 0.5 L fully-perforated pan. The coating process conditions used are shown in Table 11.

TABLE 11

Process conditions used for the coating application of Example 3

| parameter | value |
|---|---|
| Inlet temperature (° C.) | 60 |
| Exhaust temperature (° C.) | 45 |
| Spray rate (g/min) | 4 |
| Atomizing air pressure (bar) | 2 |
| Spray nozzle diameter (mm) | 0.7 |
| Process air flow (m³/h) | 76 |
| Pan speed (rpm) | 35 |
| Coating solids (% w/w) | 20 |

The multivitamin tablets of this example contained a high level of phytosterols, a waxy component, in their composition, making them a challenging substrate to coat and achieve film adhesion. The resultant coated tablets were uniformly colored and had excellent logo clarity.

Example 4

The coating of Example 2 was prepared at 22.5% solids in water. This coating suspension was used to coat multivitamin tablets in a Vector LDCS coater fitted with a 2.5 L fully-perforated pan according to the process conditions shown in Table 12.

TABLE 12

Process conditions used for the coating application of Example 4

| parameter | value |
|---|---|
| Inlet temperature (° C.) | 60 |
| Exhaust temperature (° C.) | 42 |
| Spray rate (g/min) | 11 |
| Atomizing air pressure (bar) | 1.8 |
| Pattern air pressure (bar) | 2.0 |
| Spray nozzle diameter (mm) | 1.0 |
| Process air flow (m$^3$/h) | 102 |
| Pan speed (rpm) | 23 |
| Coating solids (% w/w) | 22.5 |

Figure 9A:
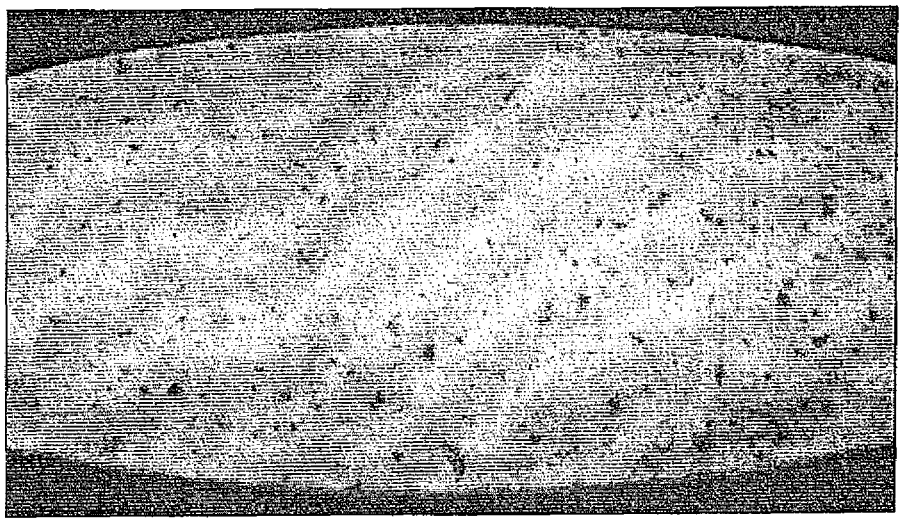
FIG. 9A-B are micrographs of coated tablet cross-sections produced in accordance with Example 4.
Figure 9B:
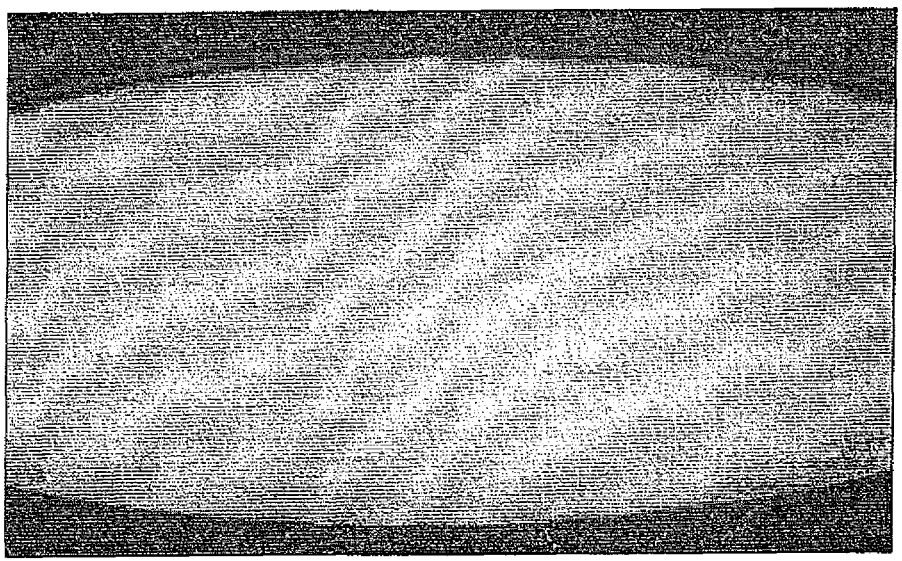

The uncoated multivitamin tablets had a speckled appearance (FIG. 9A). The coating of this Example completely masked the underlying color of the multivitamin tablet and produced a uniformly colored coated tablet (FIG. 9B).

Example 5

A coating formula of this invention was developed and contained the composition shown in Table 13. A suspension of this coating was made at 18% total solids in water.

TABLE 13

Coating formula of Example 5

| ingredient | | dry-basis addition level (w/w) |
|---|---|---|
| HPMC | type 2910, 6 cP | 27.5% |
| copovidone | Plasdone ® S-630 | 21.0% |
| polyethylene glycol | type 3350 | 9.5% |
| polydextrose | Litesse ® Two | 14.0% |
| medium-chain triglycerides | Miglyol ® 810 | 3.00% |
| titanium dioxide | | 21.0% |
| FD&C Blue No. 2 Lake (13%) | | 0.8% |
| FD&C Blue No. 1 Lake (12%) | | 3.2% |
| total | | 100.0% |

The coating of Example 5 was applied to 14.7 kg of caplet-shaped tablets containing 500 mg of paracetamol with 25 mg of diphenhydramine HCl. The coating was applied using a CompuLab Coater (Thomas Engineering) fitted with a 24-inch fully-perforated pan and 2 1/4JAU spray nozzles (Spraying Systems). The coating process conditions used are shown in Table 14.

TABLE 14

Process conditions used for the coating application of Example 5

| parameter | value |
|---|---|
| Inlet temperature (° C.) | 77 |
| Exhaust temperature (° C.) | 52 |
| Spray rate (g/min) | 58 |
| Atomizing air pressure (bar) | 3.4 |
| Process air flow (m$^3$/h) | 680 |
| Pan speed (rpm) | 10-12 |
| Coating solids (% w/w) | 18 |

The resulting coated tablets were smooth, uniformly colored and free from defects.

Changes may be made by persons skilled in the art in the compositions and/or in the steps or the sequence of steps of the method of manufacture described herein without departing from the spirit and scope of the invention as defined in the following claims.

What is claimed is:

1. A coating composition having total solids content of at least about 18% comprising:
from 25% to 66% of the water-soluble cellulose ether hydroxypropylmethyl cellulose (HPMC), from 0.5% to 60% of poly(N-vinyl-2-pyrrolidone-co-vinyl acetate) (PVP/VA) copolymer containing from 55% N-vinyl-2-pyrrolidone:45% vinyl acetate to 99% N-vinyl-2-pyrrolidone:1% vinyl acetate, from 0.1% to 45% of film forming agent polydextrose and from 6% to 22% of medium-chain triglycerides.

2. The composition of claim 1 wherein the total solids content is 20% (w/w) or more.

3. The composition of claim 2 wherein the total solids content is 25% (w/w) or more.

4. A method of coating solid substances comprising the steps of (a) creating a coating suspension comprising any of the compositions of claims 1-3, (b) forming a layer on said solid substance by applying said coating suspension, and (c) drying said layer on said solid substance.

5. The method of claim 4 wherein said solid substance is an agricultural, nutritional or pharmaceutical solid.

6. A coated product produced by a method comprising the steps of (a) creating a coating suspension comprising the composition of claim 1, (b) forming a layer on a solid substance by applying said coating suspension, and (c) drying said layer on said solid substance.

7. The coated product of claim 6 that is a coated agricultural, coated nutritional or coated pharmaceutical product.

* * * * *